(12) United States Patent
Kobayashi et al.

(10) Patent No.: US 9,506,862 B2
(45) Date of Patent: ***Nov. 29, 2016

(54) WELDED PORTION INSPECTION APPARATUS AND INSPECTION METHOD THEREOF

(71) Applicant: TOYOTA JIDOSHA KABUSHIKI KAISHA, Toyota-shi, Aichi-ken (JP)

(72) Inventors: Hiroomi Kobayashi, Okazaki (JP); Masashi Furukawa, Toyota (JP); Keisuke Uchida, Nagoya (JP); Yoshinori Shibata, Nagoya (JP); Atsushi Kawakita, Miyoshi (JP); Hiroaki Kishi, Toyota (JP); Eiji Akamatsu, Toyota (JP); Yuta Iwamoto, Toyota (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/780,584

(22) PCT Filed: Mar. 28, 2014

(86) PCT No.: PCT/IB2014/000451
§ 371 (c)(1),
(2) Date: Sep. 28, 2015

(87) PCT Pub. No.: WO2014/155191
PCT Pub. Date: Oct. 2, 2014

(65) Prior Publication Data
US 2016/0061727 A1    Mar. 3, 2016

(30) Foreign Application Priority Data

Mar. 29, 2013  (JP) ................................. 2013-073202

(51) Int. Cl.
*G01N 21/55* (2014.01)
*B23K 26/03* (2006.01)
*B23K 26/22* (2006.01)
*G01N 33/20* (2006.01)

(52) U.S. Cl.
CPC ............. *G01N 21/55* (2013.01); *B23K 26/032* (2013.01); *B23K 26/082* (2015.10); *B23K 26/22* (2013.01); *G01N 33/206* (2013.01)

(58) Field of Classification Search
CPC .. G01N 21/553; G01N 21/55; G01N 21/554; G01N 21/474; G01N 21/57
USPC .......................................................... 356/445
See application file for complete search history.

(56) References Cited

U.S. PATENT DOCUMENTS

| 4,572,941 A | 2/1986 | Sciaky et al. |
| 5,155,329 A * | 10/1992 | Terada ................. B23K 31/125 219/121.63 |
| 5,651,903 A | 7/1997 | Shirk |
| 6,937,329 B2 | 8/2005 | Esmiller |
| 8,506,872 B2 * | 8/2013 | Hokoda .............. B29C 65/1635 156/272.8 |
| 2002/0158053 A1 | 10/2002 | Kessler et al. |
| 2011/0215074 A1* | 9/2011 | Wang ..................... B23K 9/091 219/121.64 |

FOREIGN PATENT DOCUMENTS

| JP | 03-080596 B2 | 12/1991 |
| JP | 2008-087056 A | 4/2008 |
| JP | 2008-272767 A | 11/2008 |
| JP | 2014-198345 A | 10/2014 |
| WO | 2014/155190 A2 | 10/2014 |

* cited by examiner

*Primary Examiner* — Tarifur Chowdhury
*Assistant Examiner* — Md M Rahman
(74) *Attorney, Agent, or Firm* — Sughrue Mion, PLLC

(57) ABSTRACT

A welding laser beam (L1) is radiated along welding loci (C11, C12) set in workpieces (W1, W2), or an inspection laser beam (L5) is radiated along scanning loci (C51, C52) set in a molten pool (Y1) of the workpieces (W1, W2) that are molten by radiation of the welding laser beam (L1), a returned light beam (L2) including reflection light from the molten pool (Y1) of the workpieces, vapor light caused due to melting and evaporation of the workpieces, and thermal radiation light emitted from the molten pool (Y1) of the workpieces is received, and a welding state of a welded portion of the workpieces is inspected based on an intensity change of the returned light beam (L2) thus received.

6 Claims, 13 Drawing Sheets

<HOLED WELD>

<ONE-PIECE DEPRESSED WELD>

F I G . 12
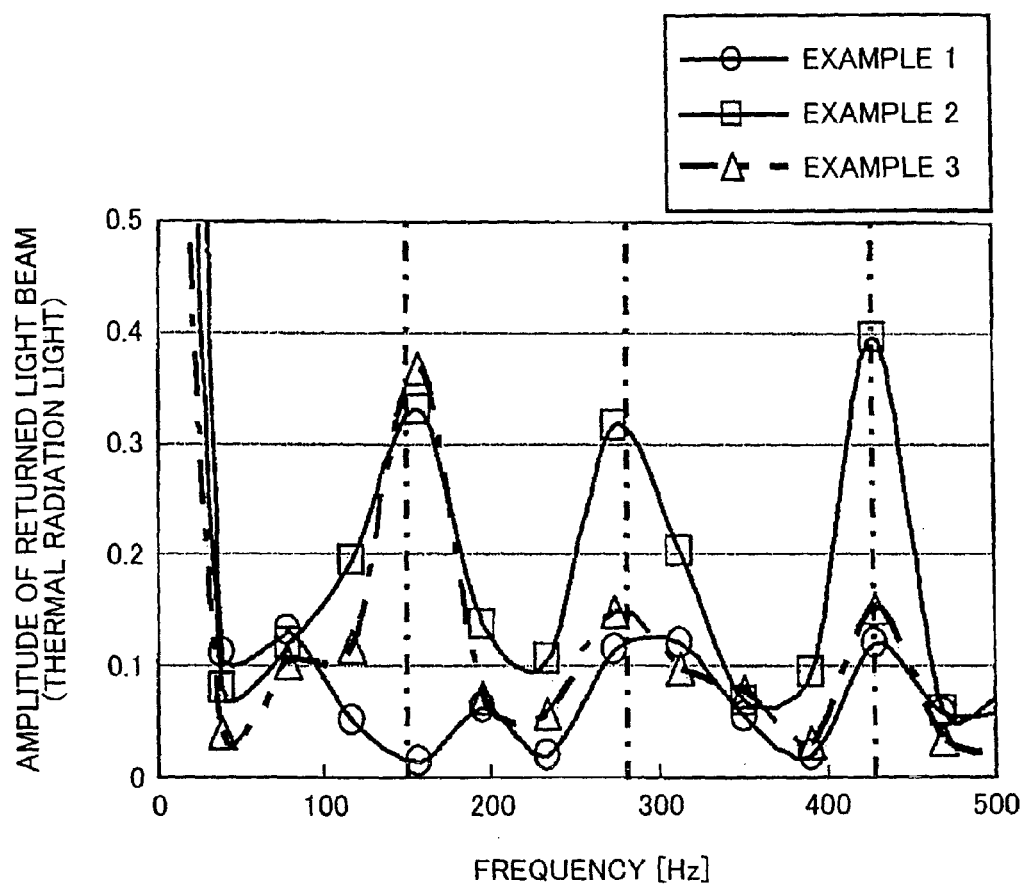

WELDED PORTION INSPECTION APPARATUS AND INSPECTION METHOD THEREOF

BACKGROUND OF THE INVENTION

1. Field of the Invention

The present invention relates to a welded portion inspection apparatus and an inspection method thereof, and relates to an inspection apparatus that inspects a welding state of a welded portion formed at the time when a plurality of workpieces is welded by a laser beam, for example, and an inspection method thereof.

2. Description of Related Art

When two steel sheets are put on top of one another and laser beam welding is performed thereon, a quality evaluation is performed on a welded portion formed by the laser beam welding. As an example of such a quality evaluation on the welded portion formed by the laser beam welding, Japanese Patent Application Publication No. 2008-87056 (JP 2008-87056 A) describes a technique to perform a quality evaluation of laser beam welding by use of reflection light of a laser beam.

In a laser beam welding quality determination system described in JP 2008-87056 A, a YAG laser is radiated from a laser torch, for example, and laser reflection light is received by first light receiving output means from a forward-diagonally upward side of a welding proceeding direction. Further, welding light including vapor light (plume) and the laser reflection light is received by second light receiving output means in a direction coaxial to a radiation direction of the laser beam. The laser reflection light and the welding light that are received simultaneously in two predetermined directions are converted into electrical signals according to their respective intensities. This system determines a welding quality based on the signal intensities of the electrical signals or changes thereof.

According to the laser beam welding quality determination system described in JP 2008-87056 A, the laser reflection light and the welding light are received simultaneously in two predetermined directions different from each other and their respective light receiving signal intensities are compared with a threshold set appropriately. Hereby, it is possible to determine occurrence of any one of the following various types of poor welding: weld shrinkage (underfill) in which a weld bead hollows to bury a gap between steel sheets; unjoined weld in which upper and lower steel sheets are not joined due to an excessively large gap between the steel sheets; depressed weld in which a bead is depressed similarly due to an excessively large gap between steel sheets; and molten weld in which a bead disappears accidentally due to fluctuation of a thermal balance; and holed weld.

However, in the laser beam welding quality determination system described in JP 2008-87056 A, in a case where the laser torch is apart from workpieces (steel sheets), for example, the electrical signals obtained from the received laser reflection light and welding light become weak. On that account, determination accuracy of poor welding may decrease. Particularly, in the depressed weld in which a bead is depressed in the laser beam welding, those changes of the electrical signals which are caused due to poor welding decrease. This may cause such a case where poor welding in the workpieces cannot be detected minutely. Further, it is known that vapor light caused due to melting and evaporation of the workpieces and thermal radiation light emitted from a molten pool of the workpieces change according to a workpiece temperature, and the electrical signals obtained from the received laser reflection light and the welding light and the threshold to determine the quality of the laser beam welding change according to the workpiece temperature. Because of this, in a case where the workpiece temperature largely fluctuates in the laser beam welding, the determination accuracy of the poor welding of the workpieces may further decreases.

SUMMARY OF THE INVENTION

The present invention provides a welded portion inspection apparatus that is able to minutely inspect a welding state of a welded portion of workpieces in remote welding in which welding is performed such that the workpieces are spaced from a laser torch, and an inspection method thereof.

A first aspect of the invention relates to a welded portion inspection apparatus that inspects a welding state of a welded portion formed at the time when a plurality of workpieces is welded. The welded portion inspection apparatus includes: a radiation portion that radiates a welding laser beam along a welding locus set in the workpieces so as to weld the workpieces, or radiates an inspection laser beam along a scanning locus set in a molten pool of the workpieces that are molten by the welding laser beam; a light-receiving portion that receives a returned light beam including at least one of reflection light of the welding laser beam or the inspection laser beam radiated by the radiation portion, the reflection light being reflected from the molten pool of the workpieces, vapor light caused due to melting and evaporation of the workpieces, and thermal radiation light emitted from the molten pool of the workpieces; and an inspection portion that inspects a welding state of the welded portion of the workpieces based on an intensity change of the returned light beam received by the light-receiving portion at the time when the welding laser beam is radiated along the welding locus or at the time when the inspection laser beam is radiated along the scanning locus.

According to the above aspect, the welding state of the welded portion of the workpieces is inspected based on the intensity change of the returned light beam received by the light-receiving portion at the time when the welding laser beam is radiated along the welding locus or at the time when the inspection laser beam is radiated along the scanning locus. Accordingly, in a case of remote welding in which welding is performed such that the radiation portion is spaced from the workpieces, for example, even if an electrical signal obtained from the returned light beam received by the light-receiving portion is weak or even if an intensity of the returned light beam received by the light-receiving portion changes according to a change of a workpiece temperature, it is possible to minutely inspect the welding state of the welded portion formed in the workpieces.

Further, in the above aspect, the radiation portion may radiate the welding laser beam several times along the same welding locus or may radiate the inspection laser beam several times along the same scanning locus. The inspection portion may inspect the welding state of the welded portion of the workpieces based on a periodicity of the intensity change of the returned light beam at the time when the welding laser beam is radiated along the same welding locus or at the time when the inspection laser beam is radiated along the same scanning locus.

According to the above aspect, the welding state of the welded portion of the workpieces is inspected based on the periodicity of the intensity change of the returned light beam at the time when the welding laser beam is radiated several times along the same welding locus or at the time when the inspection laser beam is radiated several times along the same scanning locus. Accordingly, even if an electrical signal obtained from a returned light beam at the time when the welding laser beam is radiated once along the welding locus or at the time when the inspection laser beam is radiated once along the scanning locus is weak or even if the electrical signal obtained from the returned light beam includes noise, it is possible to restrain a decrease of inspection accuracy due to the noise included in the returned light beam or the like. As a result, it is possible to increase the inspection accuracy of the welding state of the welded portion.

Further, in the above aspect, a scanning period of the welding laser beam at the time when the welding laser beam is radiated along the same welding locus, or a scanning period of the inspection laser beam at the time when the inspection laser beam is radiated along the same scanning locus may be the same as an unique period of the intensity change of the returned light beam which is obtained when the welding state of the welded portion is normal.

A liquid level of the molten pool formed in the workpieces by radiation of the welding laser beam vibrates at the same frequency as a unique frequency of the molten pool. Therefore, even if the welding state of the welded portion is normal, the intensity of the returned light beam received by the light-receiving portion changes periodically. According to the above aspect, the scanning period of the welding laser beam or the inspection laser beam is the same as that unique period of the intensity change of the returned light beam which is obtained when the welding state of the welded portion is normal. Accordingly, it is possible to easily specify that periodic intensity change of the returned light beam which is caused due to radiation of the welding laser beam, from the intensity change of the returned light beam received by the light-receiving portion, thereby making it possible to minutely specify that intensity change of the returned light beam which is caused due to poor welding. This makes it possible to further increase the inspection accuracy of the welding state of the welded portion of the workpieces.

Note that the scanning period of the welding laser beam or the inspection laser beam is a time during which the welding laser beam or the inspection laser beam scans a welding locus or a scanning locus having a predetermined length once, in a case where the welding laser beam is radiated several times along the same welding locus or the inspection laser beam is radiated several times along the same scanning locus. That is, the scanning period is a time obtained by dividing the length of the welding locus irradiated with the welding laser beam by a scanning speed of the welding laser beam, or a time obtained by dividing the length of the scanning locus irradiated with the inspection laser beam by a scanning speed of the inspection laser beam.

Further, in the above aspect, the inspection portion may inspect the welding state of the welded portion of the workpieces by performing Fourier transform or differentiation on an intensity of the returned light beam.

According to the above aspect, Fourier transform or differentiation is performed on that intensity of the returned light beam which includes the periodic intensity change caused due to radiation of the welding laser beam. Hereby, it is possible to easily specify that periodic intensity change of the returned light beam which is caused due to radiation of the welding laser beam, from the intensity change of the returned light beam, thereby making it possible to minutely specify that intensity change of the returned light beam which is caused due to poor welding. This makes it possible to still more increase the inspection accuracy of the welding state of the welded portion of the workpieces.

Further, a second aspect of the invention relates to a welded portion inspection method that inspects a welding state of a welded portion formed at the time when a plurality of workpieces is welded. The welded portion inspection method includes radiating a welding laser beam along a welding locus set in the workpieces so as to weld the workpieces, or radiating an inspection laser beam along a scanning locus set in a molten pool of the workpieces that are molten by the welding laser beam; receiving a returned light beam including at least one of reflection light of the welding laser beam or the inspection laser beam which is reflected from the molten pool of the workpieces, vapor light caused due to melting and evaporation of the workpieces, and thermal radiation light emitted from the molten pool of the workpieces; and inspecting a welding state of the welded portion of the workpieces based on an intensity change of the returned light beam received at the time when the welding laser beam is radiated along the welding locus or at the time when the inspection laser beam is radiated along the scanning locus.

According to the above aspect, the welding state of the welded portion of the workpieces is inspected based on the intensity change of the returned light beam received at the time when the welding laser beam is radiated along the welding locus or at the time when the inspection laser beam is radiated along the scanning locus. Accordingly, in a case of remote welding in which welding is performed such that a laser radiation portion is spaced from the workpieces, for example, even if an electrical signal obtained from a received returned light beam is weak or even if an intensity of a received returned light beam changes according to a change of a workpiece temperature, it is possible to minutely inspect a welding state of a welded portion formed in the workpieces.

As understood from the above description, the first and second aspects of the invention have such a simple configuration that in a case where a plurality of workpieces is welded, a welding state of a welded portion of the workpieces is inspected based on an intensity change of a returned light beam received at the time when a welding laser beam is radiated along a welding locus or at the time when an inspection laser beam is radiated along a scanning locus. Accordingly, even if an electrical signal obtained from the returned light beam is weak or even if an intensity of the returned light beam changes according to a change of a workpiece temperature, it is possible to minutely inspect the welding state of the welded portion of the workpieces.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 12 is a view illustrating a relationship between frequency and amplitude in the returned light beams of the inspection samples according to Examples 1 to 3.

DETAILED DESCRIPTION OF EMBODIMENTS

The following describes embodiments of a welded portion inspection apparatus and an inspection method thereof according to the present invention, with reference to the drawings.

[Embodiment 1 of Welded Portion Inspection Apparatus]

Figure 1:
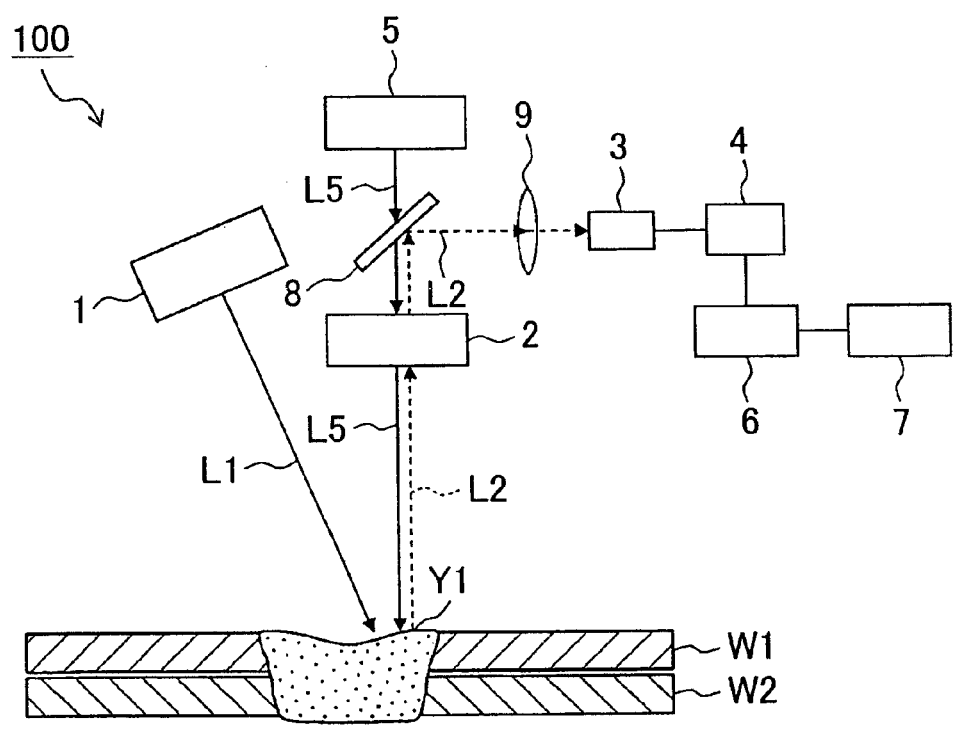
FIG. 1 is an overall configuration diagram schematically illustrating an overall configuration of Embodiment 1 of a welded portion inspection apparatus of the present invention.
Figure 2:
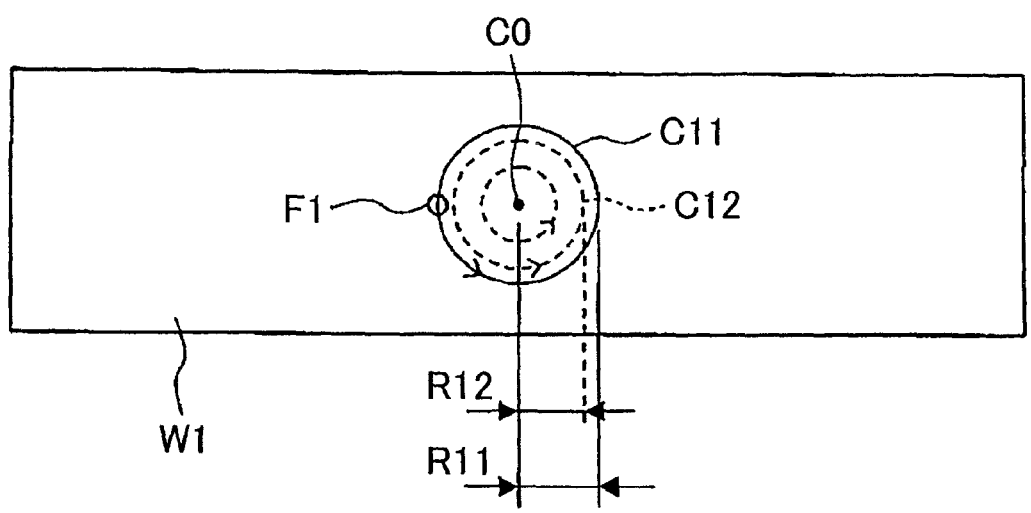
FIG. 2 is a top view to describe a form of radiation of a welding laser beam from a welding radiation portion of the inspection apparatus as illustrated in FIG. 1.
Figure 3:
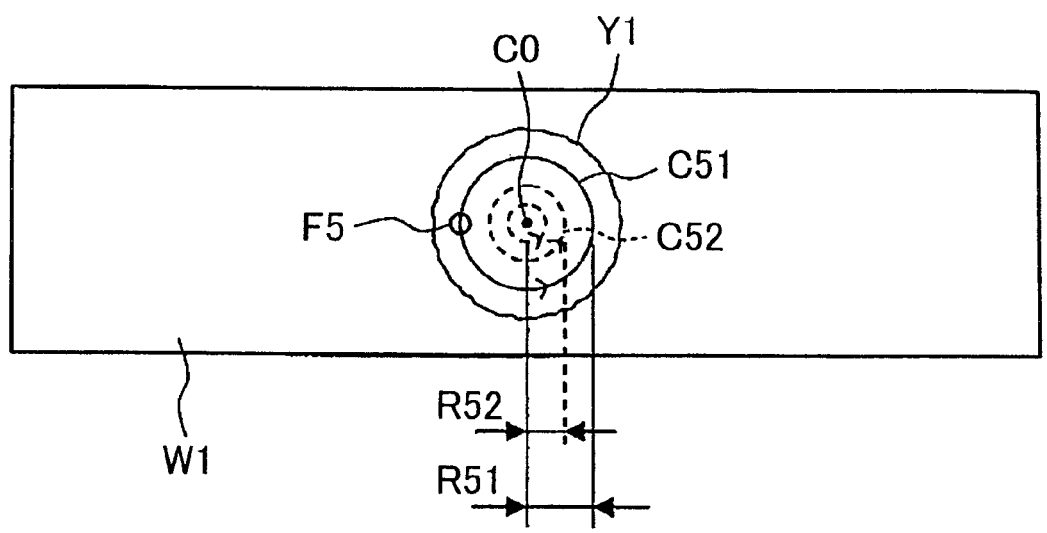
FIG. 3 is a top view to describe a form of radiation of an inspection laser beam from an inspection radiation portion of the inspection apparatus as illustrated in FIG. 1.

Initially described is Embodiment 1 of the welded portion inspection apparatus of the present invention with reference to FIGS. 1 to 3.

FIG. 1 is an overall configuration diagram schematically illustrating an overall configuration of Embodiment 1 of the welded portion inspection apparatus of the present invention. Further, FIG. 2 is a top view to describe a form of radiation of a welding laser beam from a welding radiation portion of the inspection apparatus as illustrated in FIG. 1, and FIG. 3 is a top view to describe a form of radiation of an inspection laser beam from an inspection radiation portion of the inspection apparatus.

An inspection apparatus 100 illustrated in FIG. 1 is mainly constituted by a welding radiation portion 1, an inspection radiation portion 5, a light-receiving portion 2, a conversion portion 3, an amplifier 4, an inspection portion 6, and a CRT (Cathode Ray Tube) 7.

In order to weld two workpieces (e.g., steel sheets) W1, W2 put on top of one another or disposed slightly spaced from each other, the welding radiation portion 1 radiates a welding laser beam (e.g., a YAG laser having a predetermined laser wavelength) L1 to the two workpieces W1, W2. More specifically, as illustrated in FIG. 2, the welding radiation portion 1 rotates a focal point F1 of the welding laser beam L1 several times along a generally round-shaped welding locus C11 having a radius R11 set in the workpiece W1, so as to radiate the welding laser beam L1 several times on the welding locus C11. Subsequently, the welding radiation portion 1 moves the focal point F1 of the welding laser beam L1 inside the welding locus C11, and rotates the focal point F1 of the welding laser beam L1 several times along a generally round-shaped welding locus C12 which has a radius R12 that is smaller than the radius R11 and which is coaxial to the welding locus C11, so as to radiate the welding laser beam L1 several times on the welding locus C12. By repeating such a radiation step of the welding laser beam L1, a generally round-shaped welded portion is formed in the workpieces W1, W2, thereby joining the workpieces W1, W2 by welding (also referred to as Laser Screw Welding). Note that a center C0 of the welding locus C11 or the welding locus C12 is a welding center of the welded portion formed in the workpieces W1, W2.

Here, by radiation of the welding laser beam L1 from the welding radiation portion 1, a molten pool Y1 where the workpieces W1, W2 are molten is formed on right and left sides of the welding laser beam L1 and behind the welding laser beam L1 in a traveling direction of the welding laser beam L1. In Embodiment 1, since the welding laser beam L1 is radiated along the generally round-shaped welding loci C1, C2 as described above, a generally round-shaped molten pool Y1 is formed in the workpieces W1, W2.

As illustrated in FIG. 1, the inspection radiation portion 5 radiates an inspection laser beam L5 to the molten pool Y1 in a molten state via an optical system 8 and the light-receiving portion 2. More specifically, as illustrated in FIG. 3, the inspection radiation portion 5 rotates a focal point F5 of the inspection laser beam L5 several times at a generally constant speed along a generally round-shaped scanning locus C51 having a radius R51 set inside an outer edge of the molten pool Y1, so as to radiate the inspection laser beam L5 several times on the scanning locus C51. Subsequently, the inspection radiation portion 5 moves the focal point F5 of the inspection laser beam L5 inside the scanning locus C51, and rotates the focal point F5 of the inspection laser beam L5 several times along a generally round-shaped scanning locus C52 which has a radius R52 that is smaller than the radius R51 and which is coaxial to the scanning locus C51, so as to radiate the inspection laser beam L5 several times on the scanning locus C52. By repeating such a radiation step of the inspection laser beam L5, the inspection radiation portion 5 radiates the inspection laser beam L5 to a whole of the generally round-shaped molten pool Y1 formed in the workpieces W1, W2. Note that a center of the scanning loci C51, C52 is set to the aforementioned center C0 of the welding loci C11, C12, for example.

As illustrated in FIG. 1, while the inspection laser beam L5 is radiated from the inspection radiation portion 5 to the molten pool Y1, the light-receiving portion 2 receives a returned light beam L2 including reflection light of the inspection laser light L5 which is reflected from the molten pool Y1 of the workpieces W1, W2, vapor light (plasma light) caused due to melting and evaporation of the workpieces W1, W2, thermal radiation light (infrared light) emitted from the molten pool Y1 of the workpieces W1, W2, and the like.

The conversion portion 3 converts, into an electrical signal, the returned light beam L2 received by the light-receiving portion 2 and condensed via the optical system 8 and a condenser lens 9, and outputs the electrical signal to the amplifier 4. The amplifier 4 amplifies a signal intensity of the electrical signal output from the conversion portion 3, and transmits it to the inspection portion 6.

The inspection portion 6 performs signal processing on the electrical signal transmitted from the amplifier 4, and inspects a welding state of the welded portion formed in the workpieces W1, W2. More specifically, when the inspection laser beam L5 is radiated to the molten pool Y1 from the inspection radiation portion 5 several times along the scanning loci C51, C52, the inspection portion 6 detects an intensity change of the returned light beam L2 received by the light-receiving portion 2. Then, the inspection portion 6 inspects the welding state of the welded portion formed in the workpieces W1, W2 based on a periodicity of the intensity change. Further, the inspection portion 6 transmits, to the CRT 7, a signal processing result on the electrical signal transmitted from the amplifier 4. The CRT 7 displays the signal processing result transmitted from the inspection portion 6.

[Embodiment 1 of Welded Portion Inspection Method]

Next will be described Embodiment 1 of a welded portion inspection method of the present invention by use of the welded portion inspection apparatus 100 illustrated in FIG. 1, with reference to FIGS. 4 to 7.

Figure 4:
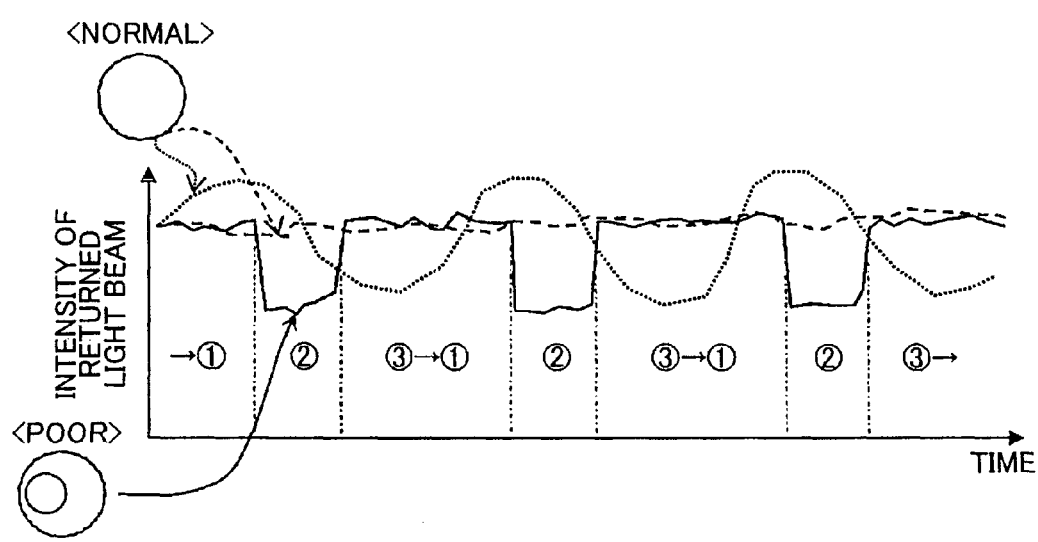
FIG. 4 is a view illustrating an example of an intensity of a returned light beam in time series.
Figure 5A:
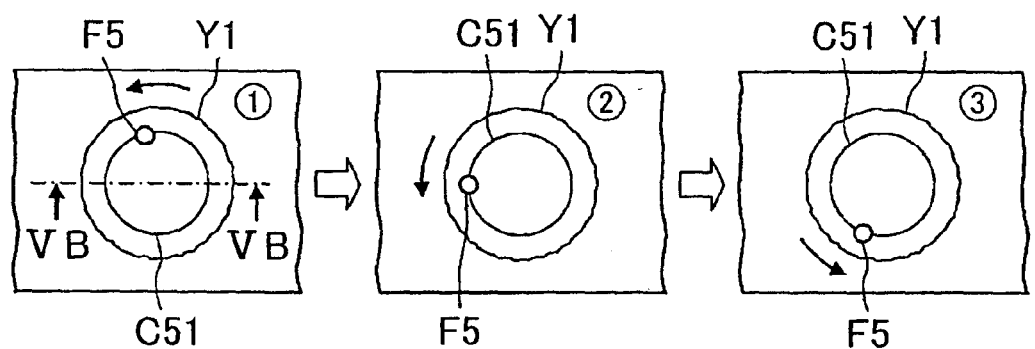
FIG. 5A is a top view to describe a relationship between a molten pool and a focal point of the inspection laser beam in a case where a welding state of a welded portion is normal.
Figure 5B:
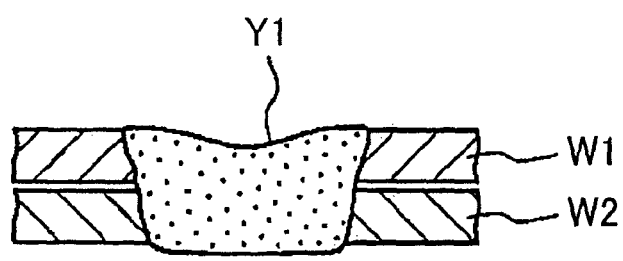
FIG. 5B is a view taken along an arrow VB-VB in FIG. 5A.
Figure 6A:
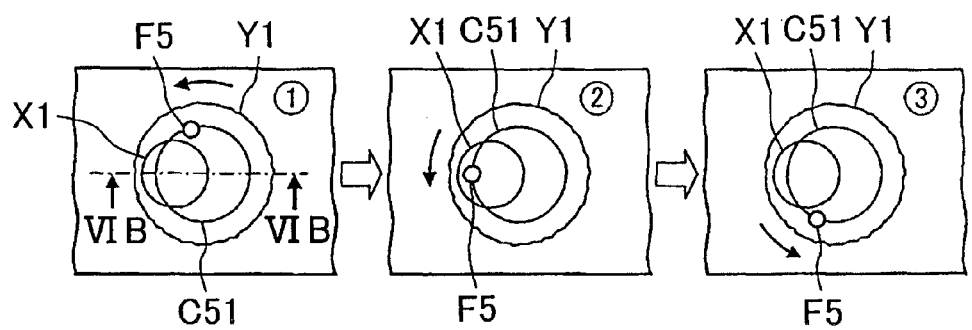
FIG. 6A a top view to describe a relationship between the molten pool and the focal point of the inspection laser beam in a case where the welding state of the welded portion is poor.
Figure 6B:
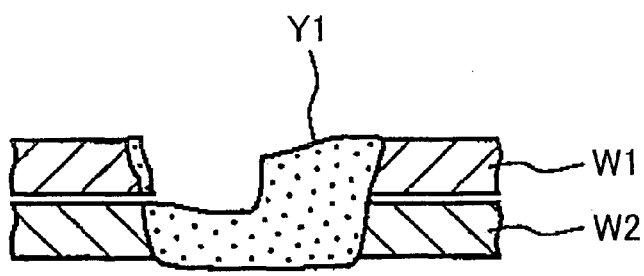
FIG. 6B is a view taken along an arrow VIB-VIB in FIG. 6A.
Figure 7:
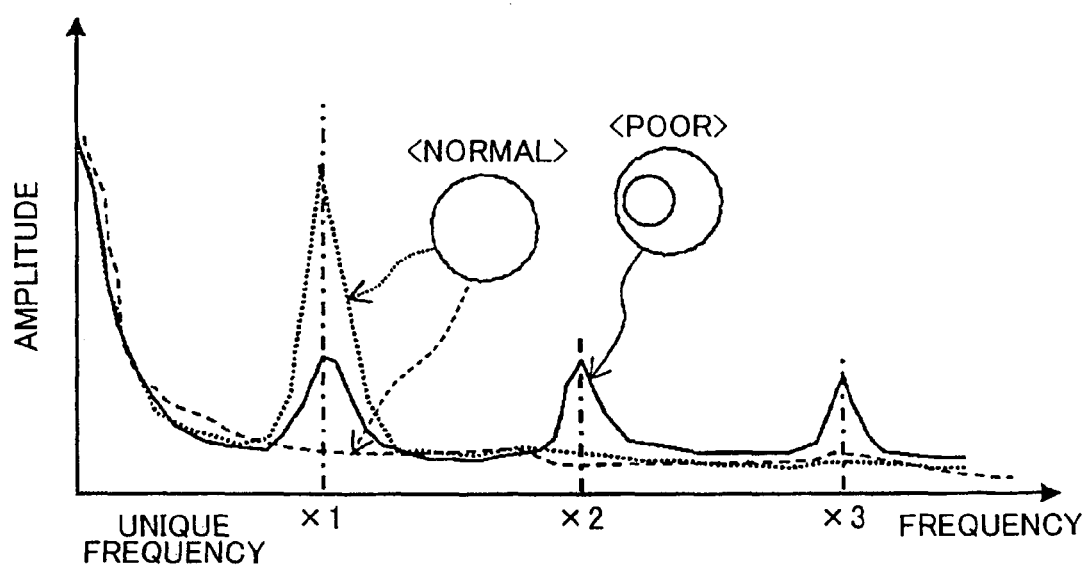
FIG. 7 is a view illustrating an example of a relationship between frequency and amplitude of the returned light beam.

FIG. 4 is a view illustrating, in time series, an example of that intensity of the returned light beam which is transmitted to the inspection portion 6 of the inspection apparatus 100 illustrated in FIG. 1. Further, FIG. 5A is a top view to describe a relationship between the molten pool and the focal point of the inspection laser beam in a case where the welding state of the welded portion is normal, and FIG. 5B is a view taken along an arrow VB-VB of FIG. 5A. Further, FIG. 6A is a top view to describe a relationship between the molten pool and the focal point of the inspection laser beam in a case where the welding state of the welded portion is poor, and FIG. 6B is a view taken along an arrow VIB-VIB of FIG. 6A. Further, FIG. 7 is a view illustrating an example of a relationship between frequency and amplitude of the returned light beam on which the signal processing is performed by the inspection portion 6.

As illustrated in FIGS. 5A and 5B, in a case where the welding state of the welded portion is normal (in a case where the workpieces W1, W2 are welded normally), when the focal point F5 of the inspection laser beam L5 is rotated several times along the generally round-shaped scanning locus C51 set in the molten pool Y1 so as to radiate the inspection laser beam L5 several times on the scanning locus C51, it is considered that intensity changes of the reflection light of the inspection laser beam L5 which is reflected from the workpieces W1, W2, the vapor light, the thermal radiation light, and the like are relatively small. On that account, as illustrated in a broken line of FIG. 4, the intensity change of the returned light beam L2 received by the light-receiving portion 2 and transmitted to the inspection portion 6 via the conversion portion 3 and the amplifier 4 is relatively small.

On the other hand, as illustrated in FIGS. 6A and 6B, in a case where the welding state of the welded portion is poor (e.g., in a case of one-piece depressed weld in which a weld bead of one of the workpieces is depressed), when the focal point F5 of the inspection laser beam L5 is rotated several times along the generally round-shaped scanning locus C51 set in the molten pool Y1 so as to radiate the inspection laser beam L5 several times on the scanning locus C51, a poor welding portion X1 exists on the scanning locus C51 of the inspection laser beam L5, so that an intensity of that reflection light of the inspection laser beam L5 which is reflected from the workpieces W1, W1 largely changes in part of the scanning locus C51. In view of this, as illustrated in a continuous line of FIG. 4, the intensity of the returned light beam L2 received by the light-receiving portion 2 and transmitted to the inspection portion 6 via the conversion portion 3 and the amplifier 4 changes in part of one scanning period (e.g., a period during which the inspection laser beam L5 goes around a scanning period C5 once) of the inspection laser beam L5, and periodically changes every scanning period of the inspection laser beam L5.

According to the inspection method of Embodiment 1, such a periodicity of the intensity change of the returned light beam L2 is detected by the inspection portion 6. Hereby, even if the electrical signal obtained from the returned light beam L2 is weak or even if the intensity of the returned light beam L2 changes according to a change of a workpiece temperature, for example, it is possible to inspect whether or not the poor welding portion X1 exists inside the outer edge of the molten pool Y1, that is, whether or not poor welding occurs in the welded portion formed in the workpieces W1, W2. Particularly, in Embodiment 1, the inspection laser beam L5 is radiated to the molten pool Y1 along the generally round-shaped scanning loci C51, C52. In view of this, it is possible to inspect whether or not a poor welding portion X1 deviating from the welding center C0 exists inside the outer edge of the molten pool Y1, or it is possible to inspect whether or not a poor welding portion X1 having a non-circular shape such as an elliptical shape or a generally polygonal shape exists inside the outer edge of the molten pool Y1.

Further, Fourier transform is performed on the intensity (see FIG. 4) of the returned light beam L2 transmitted to the inspection portion 6. In this case, as illustrated in FIG. 7, when the welding state of the welded portion is normal, an amplitude peak is not detected at a specific frequency (see a broken line in FIG. 7), and when the welding state of the welded portion is poor, amplitude peaks are detected at specific frequencies (three frequencies in FIG. 7) (see a continuous line in FIG. 7). Thus, by performing Fourier transform on the intensity of the returned light beam L2, it is possible to easily detect that intensity change of the returned light beam which is caused due to a poor welding state of the welded portion. This makes it possible to more minutely inspect whether or not poor welding occurs in the welded portion formed in the workpieces W1, W2.

Here, a liquid level of the molten pool Y1 formed in the workpieces W1, W2 by radiation of the welding laser beam L1 vibrates periodically, and it is found by the inventor(s) of the present invention that even in a case where the welding state of the welded portion is normal, the intensity of the returned light beam L2 changes periodically. That is, it is considered that one of the frequencies at which the amplitude peaks are detected in FIG. 7 is a unique frequency to the intensity change of the returned light beam L2 which unique frequency is obtained when the welding state of the welded portion is normal.

In view of this, when the inspection laser beam L5 is radiated along the generally round-shaped scanning loci C51, C52 set in the molten pool Y1, a scanning speed of the inspection laser beam L5 is adjusted, for example, so that the scanning period (e.g., a period during which the inspection laser beam L5 goes around the scanning locus C51 or the scanning locus C52 once) of the inspection laser beam L5 accords with a unique period of the intensity change of the returned light beam L2. This allows that intensity change of the returned light beam L2 transmitted to the inspection portion 6 which is obtained when the welding state of the welded portion is normal, to be in a form of a generally sine curve (a dotted line in FIG. 4). Then, by performing Fourier transform on that intensity of the returned light beam L2 which is obtained when the welding state of the welded portion is normal, it is possible to specify a unique frequency of that intensity change of the returned light beam L2 which is obtained when the welding state of the welded portion is normal, from the frequencies at which the amplitude peaks are detected in FIG. 7 (a dotted line in FIG. 7). Note that it is also possible to specify the periodicity of the intensity change of the returned light beam L2 by performing differentiation on the intensity of the returned light beam L2, instead of Fourier transform.

When the inspection laser beam L5 is radiated along the scanning loci C51, C52 at that unique period of the intensity change of the returned light beam L2 which is obtained when the welding state of the welded portion of the workpieces W1, W2 is normal, it is possible to specify, from the frequencies at which the amplitude peaks are detected in FIG. 7, that unique frequency of the intensity change of the returned light beam L2 which is obtained when the welding state of the welded portion is normal, thereby making it possible to extract only a frequency caused due to a poor welding state of the welded portion, for example. In view of this, it is possible to further more minutely inspect whether or not the poor welding portion X1 exists inside the outer edge of the molten pool Y1, that is, whether or not poor welding occurs in the welded portion formed in the workpieces W1, W2.

Further, according to Embodiment 1, the inspection laser beam L5 is radiated along the scanning loci C51, C52 set in the molten pool Y1 formed by radiation of the welding laser beam L1. Then, the welding state of the welded portion is inspected based on the intensity change of the returned light beam L2 received by the light-receiving portion 2 at the time when the inspection laser beam L5 is radiated along the scanning loci C51, C52. Accordingly, for example, even in a case where a radiation condition of the welding laser beam L1 changes or in a case where a focal position of the welding laser beam is spaced from an occurrence position of the poor welding portion X1, it is possible to appropriately adjust a scanning condition (a scanning locus, a scanning speed, and the like) of the inspection laser beam L5. This makes it possible to minutely inspect the welding state of the welded portion formed in the workpieces.

[Embodiment 2 of Welded Portion Inspection Apparatus]

Next will be described Embodiment 2 of the welded portion inspection apparatus of the present invention with reference to FIG. 8.

Figure 8:
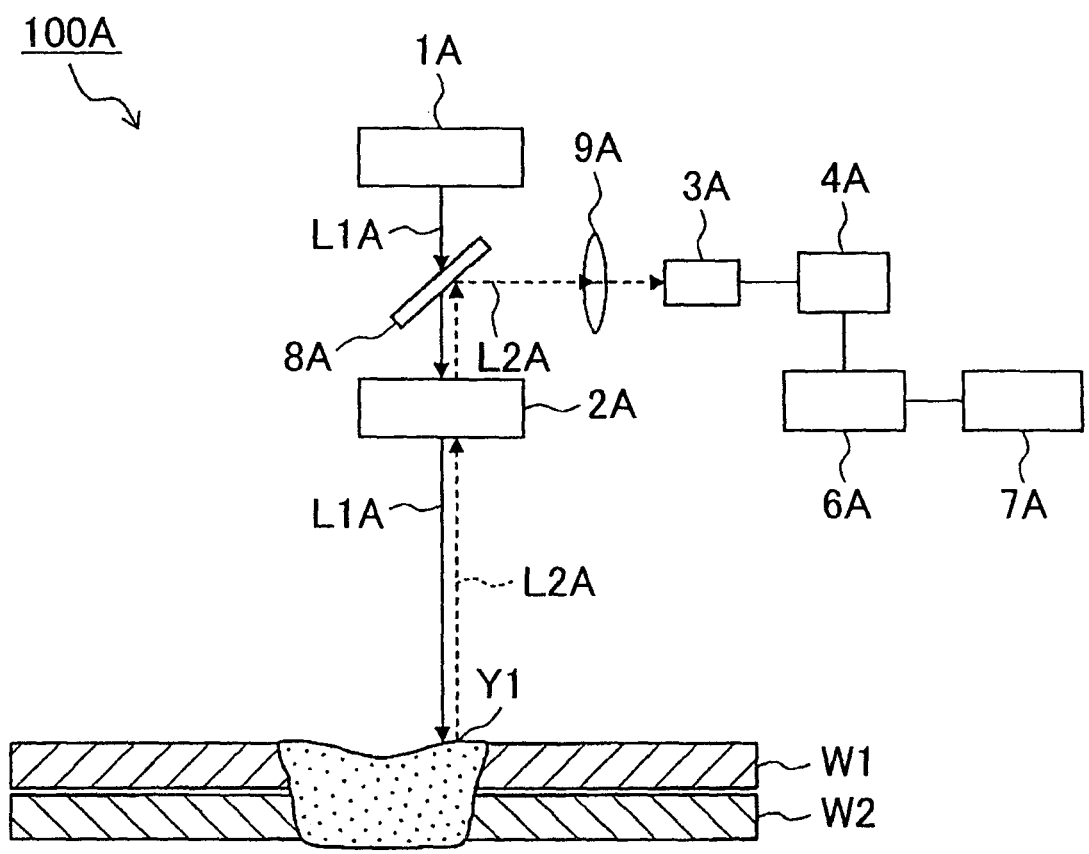
FIG. 8 is an overall configuration diagram schematically illustrating an overall configuration of Embodiment 2 of the welded portion inspection apparatus of the present invention.

FIG. 8 is an overall configuration diagram schematically illustrating an overall configuration of Embodiment 2 of the welded portion inspection apparatus of the present invention. An inspection apparatus 100A of Embodiment 2 as illustrated in FIG. 8 is different from the inspection apparatus 100 of Embodiment 1 as illustrated in FIG. 1 in that a welding state of a welded portion is inspected by use of reflection light of a welding laser beam radiated from a welding radiation portion. The other configuration is generally the same as the inspection apparatus 100 of Embodiment 1. Accordingly, constituents similar to those in Embodiment 1 have the same reference signs as those in Embodiment 1 and detailed descriptions thereof are omitted.

The inspection apparatus 100A illustrated in the figure is mainly constituted by a welding radiation portion 1A, a light-receiving portion 2A, a conversion portion 3A, an amplifier 4A, an inspection portion 6A, and a CRT 7A.

In order to weld two workpieces W1, W2 put on top of one another or disposed slightly spaced from each other, the welding radiation portion 1A radiates a welding laser beam L1A to the two workpieces W1, W2 via an optical system 8A and the light-receiving portion 2A. By radiation of the welding laser beam L1A from the welding radiation portion 1A, a molten pool Y1 where the workpieces W1, W2 are molten is formed on right and left sides of the welding laser beam L1A and behind the welding laser beam L1A in a traveling direction of the welding laser beam L1A.

The light-receiving portion 2A receives a returned light beam L2A including reflection light of the welding laser light L1A radiated from the welding radiation portion 1A, the reflection light being reflected from the molten pool Y1 of the workpieces W1, W2, vapor light (plasma light) caused due to melting and evaporation of the workpieces W1, W2, thermal radiation light (infrared light) emitted from the molten pool Y1 of the workpieces W1, W2, and the like.

The conversion portion 3A converts, into an electrical signal, the returned light beam L2A received by the light-receiving portion 2A and condensed via the optical system 8A and a condenser lens 9A, and outputs the electrical signal to the amplifier 4A. The amplifier 4A amplifies a signal intensity of the electrical signal output from the conversion portion 3A, and transmits it to the inspection portion 6A.

The inspection portion 6A performs signal processing on the electrical signal transmitted from the amplifier 4A, and inspects a welding state of the welded portion formed in the workpieces W1, W2. More specifically, the inspection portion 6A detects an intensity change of the returned light beam L2A received by the light-receiving portion 2A at the time when the welding laser beam L1A is radiated from the welding radiation portion 1A along a welding locus. Then, the inspection portion 6A inspects the welding state of the welded portion formed in the workpieces W1, W2 based on a periodicity of the intensity change. Further, the inspection portion 6A transmits, to the CRT 7A, a signal processing result on the electrical signal transmitted from the amplifier 4A. The CRT 7A displays the signal processing result transmitted from the inspection portion 6A.

Similarly to Embodiment 1 described above, in a case where the welding state of the welded portion is normal, the intensity change of the returned light beam L2A received by the light-receiving portion 2A at the time when the welding laser beam L1A is radiated along the welding locus is relatively small, and in a case where the welding state of the welded portion is poor, the intensity change is relatively large. According to Embodiment 2, such a periodicity of the intensity change of the returned light beam L2A is detected by the inspection portion 6A. Hereby, even if the electrical signal obtained from the returned light beam L2A is weak or even if the intensity of the returned light beam L2A changes according to a change of a workpiece temperature, for example, it is possible to inspect whether or not a poor welding portion X1 is formed inside an outer edge of the molten pool Y1, that is, whether or not poor welding occurs in the welded portion formed in the workpieces W1, W2.

Further, similarly to Embodiment 1, the welding laser beam L1A is radiated along the welding locus at that unique period of the intensity change of the returned light beam L2A which is obtained when the welding state of the welded portion of the workpieces W1, W2 is normal. Accordingly, it is possible to specify that unique frequency of the intensity change of the returned light beam L2A which is obtained when the welding state of the welded portion is normal, from specific frequencies at which amplitude peaks are detected by performing Fourier transform on the intensity of the returned light beam L2A, thereby making it possible to extract only a frequency caused due to a poor welding state of the welded portion, for example. In view of this, it is possible to further more minutely inspect whether or not the poor welding portion X1 exists inside the outer edge of the molten pool Y1, that is, whether or not poor welding occurs in the welded portion formed in the workpieces W1, W2.

Note that Embodiment 1 described above deals with an embodiment in which the center of the scanning locus of the inspection laser beam is set to the center of the welding locus of the welding laser beam. However, it is possible to set the center of the scanning locus of the inspection laser beam to an appropriate position in the molten pool formed by radiation of the welding laser beam.

Further, the embodiments described above deal with an embodiment in which the welding locus of the welding laser beam and the scanning locus of the inspection laser beam have a generally round shape. However, the welding locus of the welding laser beam and the scanning locus of the inspection laser beam may have a closed loop shape such as an elliptical shape or a polygonal shape, a curved or linear shape having a predetermined length, or the like. Further, in a case where a part of the welded portion in which poor welding is easy to occur is predictable, it is preferable that the welding locus of the welding laser beam and the scanning locus of the inspection laser beam be set to pass through that part.

Further, the above embodiments deal with an embodiment in which the welding laser beam and the inspection laser beam are radiated to workpieces fixed to a predetermined position. However, focal positions of the welding laser beam and the inspection laser beam may be fixed and laser beam welding may be performed on the workpieces while the workpieces are being moved appropriately. Alternatively, laser beam welding may be performed on the workpieces such that the workpieces and the focal positions of the welding laser beam and the inspection laser beam are moved relative to each other.

[Experiment on Inspection Samples to Evaluate Relationship between Intensity Change of Returned Light Beam and Welding State of Welded Portion and Results thereof]

The inventor(s) of the present invention manufactured three types of inspection samples (Examples 1 to 3) having different welding states, and performed intensity measurement of a returned light beam from each of the inspection samples so as to evaluate a relationship between an intensity change of the returned light beam and a welding state of a welded portion thereof.

<Manufacturing Method of Inspection Sample and Measurement Method of Intensity of Returned Light Beam from Inspection Sample>

Initially, the following generally describes a manufacturing method of an inspection sample and a measurement method of an intensity of a returned light beam from an inspection sample. Two workpieces each made from SCGA440 having a thickness of 0.7 mm were put on top of one another, and a welding laser beam (with an output of 1000 W and at a scanning speed of 80 m/min) was radiated several times to the workpieces along a generally round-shaped welding locus so as to form a generally round-shaped welded portion having a radius of about 2.2 mm. Subsequently, an inspection laser beam (with an output of 1000 W and at a scanning speed of 80 m/min) was radiated to go around six times along a generally round-shaped scanning locus having a radius of about 1.5 mm so as to pass through a molten pool formed in the workpieces by radiation of the welding laser beam. Then, a focal point of the inspection laser beam was moved only by about 0.5 mm, and the inspection laser beam was radiated to go around ten times along a generally round-shaped scanning locus having a radius of about 1.0 mm. Here, a returned light beam including reflection light of the welding laser beam which was reflected from the molten pool of the workpieces, vapor light caused due to melting and evaporation of the workpieces, thermal radiation light emitted from the molten pool of the workpieces, and the like was received, and a returned light beam including reflection light of the inspection laser light which was reflected from the molten pool of the workpieces, vapor light, thermal radiation light, and the like was received. The returned light beam thus received was converted into an electrical signal, and a signal intensity thereof was measured. Note that, in the returned light beam, particularly a signal intensity of the vapor light (plasma light) caused due to melting and evaporation of the workpieces was measured in this experiment.

<Results of Evaluation on Relationship between Intensity Change of Returned Light Beam and Welding State of Welded Portion according to Inspection Sample>

Figure 9A:
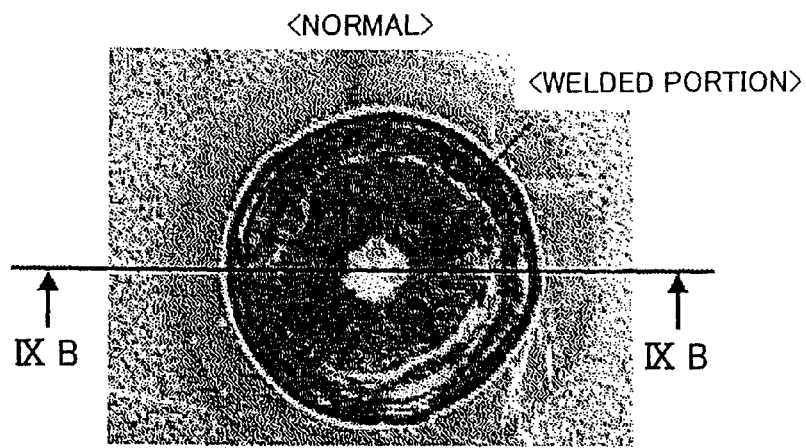
FIG. 9A is a top view enlarging and illustrating a welded portion of an inspection sample according to Example 1.
Figure 9B:
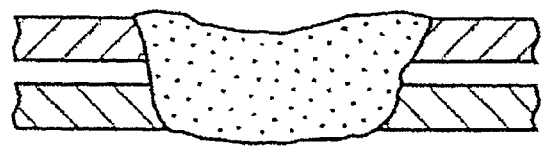
FIG. 9B is a view taken along an arrow IXB-IXB in FIG. 9A.
Figure 9C:
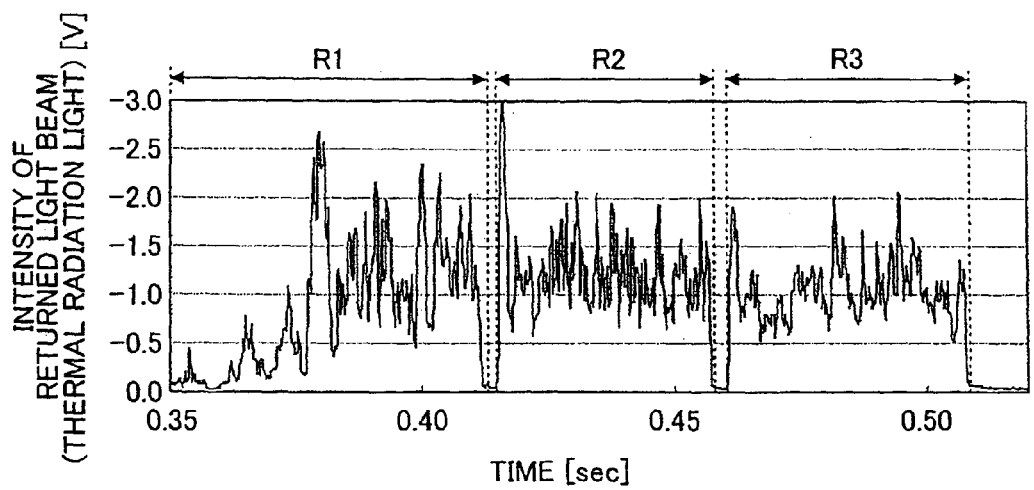
FIG. 9C is a view illustrating an intensity of a returned light beam in the inspection sample according to Example 1 in time series.
Figure 10A:
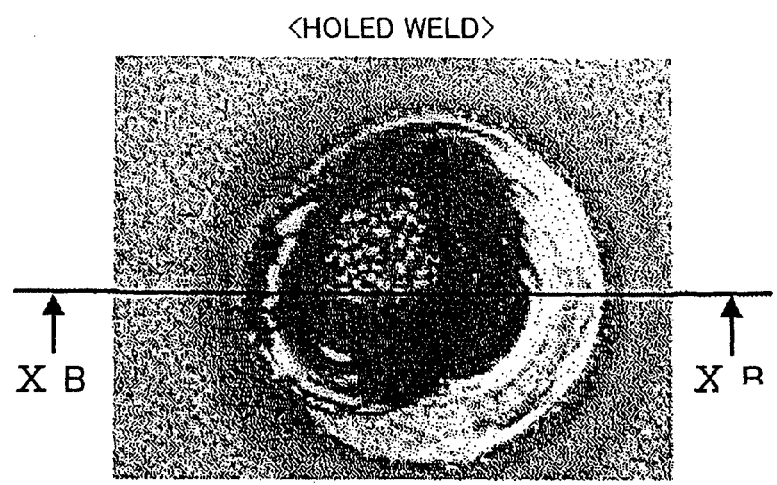
FIG. 10A is a top view enlarging and illustrating a welded portion of an inspection sample according to Example 2.
Figure 10B:
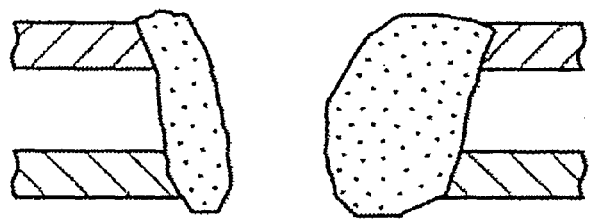
FIG. 10B is a view taken along an arrow XB-XB of FIG. 10A.
Figure 10C:
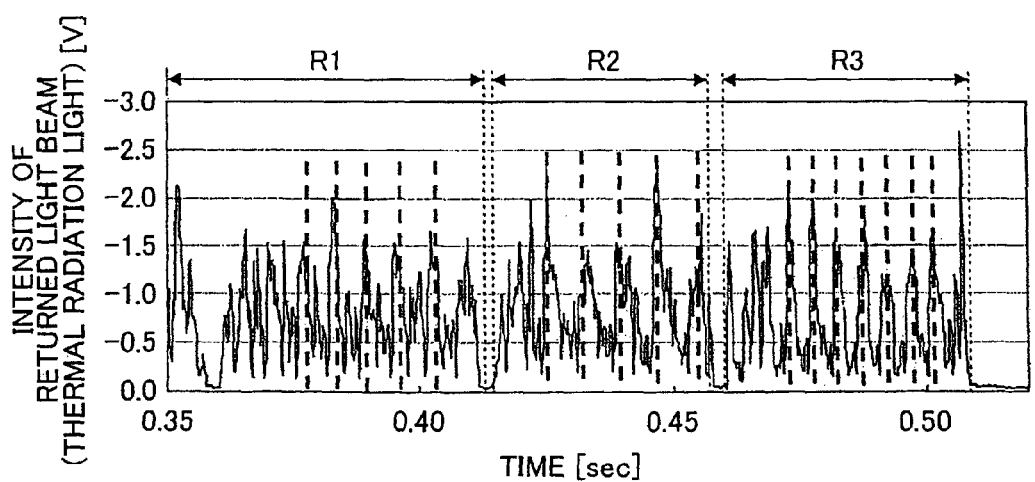
FIG. 10C is a view illustrating an intensity of a returned light beam in the inspection sample according to Example 2 in time series.

FIG. 9A is a top view enlarging and illustrating a welded portion of the inspection sample according to Example 1, FIG. 9B is a view taken along an arrow IXB-IXB in FIG. 9A, and FIG. 9C is a view illustrating an intensity of a returned light beam in the inspection sample according to Example 1 in time series. Further, FIG. 10A is a top view enlarging and illustrating a welded portion of the inspection sample according to Example 2, FIG. 10B is a view taken along an arrow XB-XB in FIG. 10A, and FIG. 10C is a view illustrating an intensity of a returned light beam in the inspection sample according to Example 2 in time series. Further, FIG. 11A is a top view enlarging and illustrating a welded portion of the inspection sample according to Example 3, FIG. 11B is a view taken along an arrow XIB-XIB in FIG. 11A, and FIG. 11C is a view illustrating an intensity of a returned light beam of the inspection sample according to Example 3 in time series.

As illustrated in FIGS. 9A to 9C, in the inspection sample of Example 1 (a welding state is normal), no periodicity was found in intensity changes of returned light beams measured in a zone R1 (0.35 to about 0.41 sec) in which the welding laser beam was radiated, in a zone R2 (about 0.41 to about 0.46 sec) in which the inspection laser beam was radiated along the scanning locus having a radius of about 1.5 mm, and in a zone R3 (about 0.46 to about 0.51 sec) in which the inspection laser beam was radiated along the scanning locus having a radius of about 1.0 mm.

In the meantime, as illustrated in FIGS. 10A to 10C, in the inspection sample of Example 2 (holed weld in which two workpieces were molten and depressed), periodicities were found in intensity changes of returned light beams measured in the zone R1 in which the welding laser beam was radiated and in the zones R2, R3 in which the inspection laser beam was radiated.

Figure 11A:
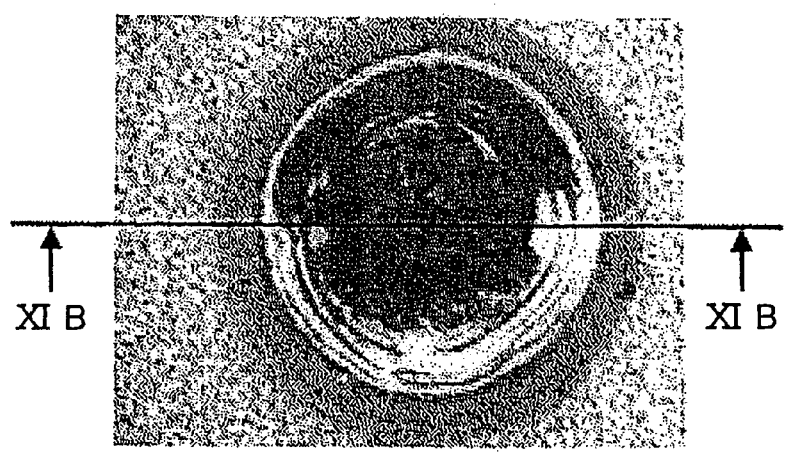
FIG. 11A is a top view enlarging and illustrating a welded portion of an inspection sample according to Example 3.
Figure 11B:
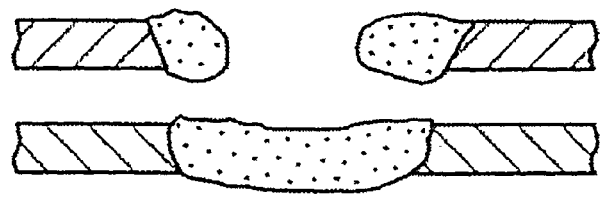
FIG. 11B is a view taken along an arrow XIB-XIB of FIG. 11A.
Figure 11C:
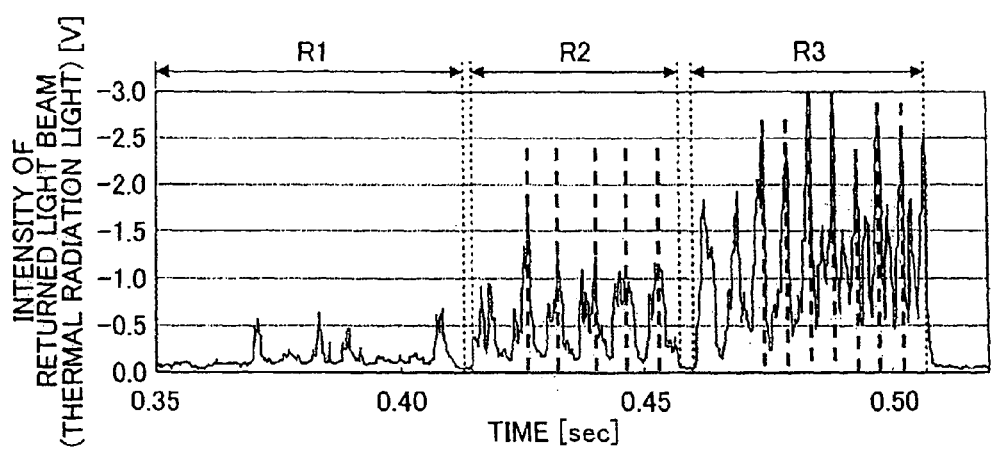
FIG. 11C is a view illustrating an intensity of a returned light beam in the inspection sample according to Example 3 in time series.

Further, as illustrated in FIGS. 11A to 11C, in the inspection sample of Example 3 (one-piece depressed weld in which one of two workpieces was molten and depressed), no periodicity was found in an intensity change of a returned light beam measured in the zone R1 in which the welding laser beam was radiated, but periodicities were found in intensity changes of returned light beams measured in the zones R2, R3 in which the inspection laser beam was radiated.

Further, FIG. 12 is a view illustrating a relationship between frequency and amplitude at the time when fast Fourier transform was performed on an intensity of the returned light beam measured in the zone R2 (about 0.41 to about 0.46 sec) in which the inspection laser beam was radiated to the inspection sample according to each of Examples 1 to 3.

As illustrated in FIG. 12, in the inspection sample of Example 1 (the welding state is normal), a large amplitude peak was not found. However, in the inspection sample of Example 2 (holed weld), large amplitude peaks were found at frequencies of integral multiples of about 141 Hz, and in the inspection sample of Example 3 (one-piece depressed weld), a large amplitude peak was found at a frequency of about 141 Hz. Note that the frequency (about 141 Hz) at which the amplitude peaks were found in the inspection samples of Examples 2 and 3 generally corresponds to a scanning frequency (1/(1.5 mm×2×3.14/(80000 mm/60 sec)) Hz) of an inspection laser beam of a scanning speed of 80 m/min at the time when the inspection laser beam was radiated along the scanning locus having a radius of about 1.5 mm.

From this experimental result, the following was demonstrated: by a simple and easy method for detecting a periodicity of an intensity change of a returned light beam to be received at the time when a welding laser beam is radiated along a welding locus or at the time when an inspection laser beam is radiated along a scanning locus, it is possible to minutely inspect a welding state of a welded portion including poor welding such as weld shrinkage in which a weld bead hollows to bury a gap between workpieces, unjoined weld in which workpieces are not joined to each other, depressed weld in which a bead is depressed, molten weld in which a bead disappears accidentally due to fluctuation of a thermal balance, holed weld, and the like.

Further, it was also found by the inventor(s) of the present invention that a liquid level of a molten pool formed in the workpieces by radiation of the welding laser beam vibrates periodically, and even in a case where the welding state of the welded portion is normal, the intensities of the returned light beams measured in the zone R1 in which the welding laser beam is radiated and in the zones R2, R3 in which the inspection laser beam is radiated periodically change.

In view of this, the inventor(s) of the present invention calculated an unique frequency of the molten pool based on a surface tension and a density of the workpieces in a molten state, a magnitude and a thickness of the molten pool formed in the workpieces, etc. The scanning speed of the inspection laser beam was adjusted so that the scanning period of the inspection laser beam accorded with an unique period of the intensity changes of the returned light beams which is calculated from the unique frequency of the molten pool, and the inspection laser beam was radiated to the workpieces.

Figure 13:
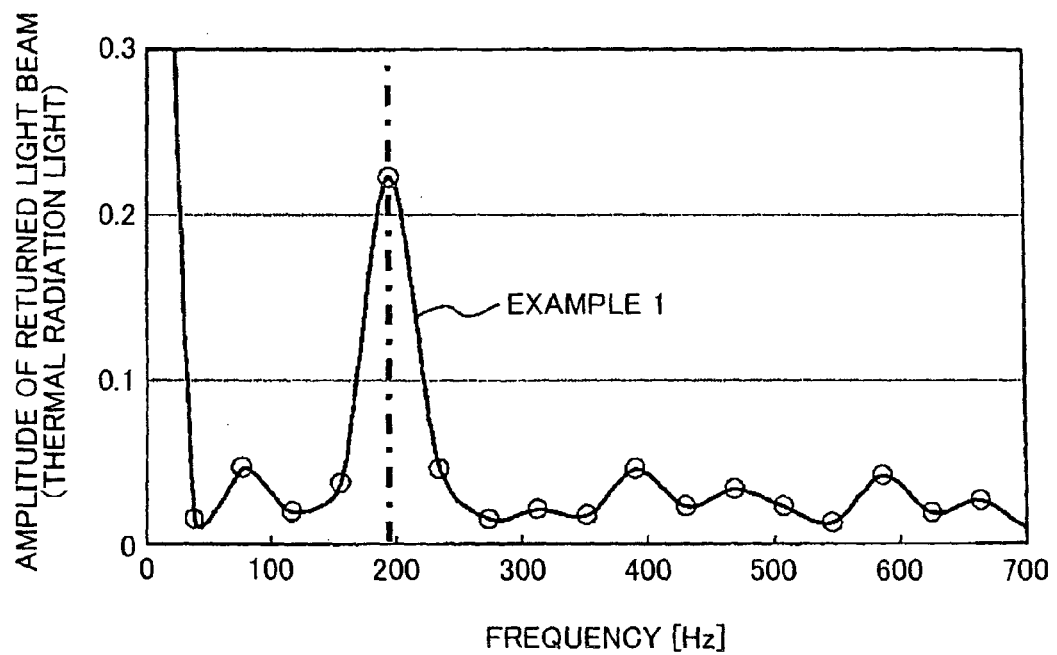
FIG. 13 is a view illustrating other examples of the relationship between frequency and amplitude in the returned light beams of the inspection samples according to Examples 1 to 3.

FIG. 13 is a view illustrating a relationship between frequency and amplitude at the time when the inspection laser beam was radiated to the molten pool in Example 1 (the welding state is normal) at the unique period of the intensity change of the returned light beam and fast Fourier transform was performed on the intensity of the returned light beam (particularly, thermal radiation light emitted from the molten pool of the workpieces) measured in the zone R2.

As illustrated in FIG. 13, even in a case where the welding state of the welded portion was normal, when fast Fourier transform was performed on the intensity of the returned light beam measured in the zone R2, a large amplitude peak was found at a specific frequency (about 195 Hz).

From this experimental result, when the welding laser beam or the inspection laser beam is radiated at that unique period of the intensity change of the returned light beam which is obtained when the welding state of the welded portion is normal, and fast Fourier transform is performed on the intensity of the measured returned light beam, it is possible to specify the unique frequency (e.g., about 195 Hz) of the intensity change of the returned light beam in the case where the welding state of the welded portion is normal. As a result, it is demonstrated that only a frequency caused due to a poor welding state of the welded portion can be detected and the welding state of the welded portion can be minutely inspected.

Thus, the embodiments of the present invention have been described with reference to the drawings, but concrete configurations of the present invention are not limited to the above embodiments. Even if there are changes of design or the like within a range that does not deviate from a gist of the present invention, they are included in the present invention.

The invention claimed is:

1. A welded portion inspection apparatus that inspects a welding state of a welded portion formed at the time when a plurality of workpieces is welded, the welded portion inspection apparatus comprising:

a laser beam radiation portion that radiates a welding laser beam along a welding locus set in the workpieces so as to weld the workpieces, or radiates an inspection laser beam along a scanning locus set in a molten pool of the workpieces that are molten by the welding laser beam;

a laser-receiving sensor that receives a returned light beam including at least one of reflection light of the welding laser beam or the inspection laser beam radiated by the laser beam radiation portion, the reflection light being reflected from the molten pool of the workpieces, vapor light caused due to melting and evaporation of the workpieces, and thermal radiation light emitted from the molten pool of the workpieces; and a measuring instrument that monitors an intensity change of the returned light beam received by the laser-receiving sensor at the time when the welding laser beam is radiated along the welding locus or at the time when the inspection laser beam is radiated along the scanning locus, in order to inspect a welding state of the welded portion of the workpieces, wherein:

the laser beam radiation portion radiates the welding laser beam several times along the same welding locus or radiates the inspection laser beam several times along the same scanning locus; and the measuring instrument inspects the welding state of the welded portion of the workpieces based on a periodicity of the intensity change of the returned light beam at the time when the welding laser beam is radiated along the same welding locus or at the time when the inspection laser beam is radiated along the same scanning locus.

2. The welded portion inspection apparatus according to claim 1, wherein:
   a scanning period of the welding laser beam at the time when the welding laser beam is radiated along the same welding locus, or a scanning period of the inspection laser beam at the time when the inspection laser beam is radiated along the same scanning locus is the same as an unique period of the intensity change of the returned light beam which is obtained when the welding state of the welded portion is normal.

3. The welded portion inspection apparatus according to claim 1, wherein:
   the measuring instrument inspects the welding state of the welded portion of the workpieces by performing Fourier transform or differentiation on an intensity of the returned light beam.

4. A welded portion inspection method for inspecting a welding state of a welded portion formed at the time when a plurality of workpieces is welded, the welded portion inspection method comprising:
   radiating a welding laser beam along a welding locus set in the workpieces so as to weld the workpieces, or radiating an inspection laser beam along a scanning locus set in a molten pool of the workpieces that are molten by the welding laser beam;
   receiving a returned light beam including at least one of reflection light of the welding laser beam or the inspection laser beam which is reflected from the molten pool of the workpieces, vapor light caused due to melting and evaporation of the workpieces, and thermal radiation light emitted from the molten pool of the workpieces; and
   inspecting a welding state of the welded portion of the workpieces based on an intensity change of the returned light beam received at the time when the welding laser beam is radiated along the welding locus or at the time when the inspection laser beam is radiated along the scanning locus, wherein:
   in the radiating of the welding laser beam or the inspection laser beam, the welding laser beam is radiated several times along the same welding locus or the inspection laser beam is radiated several times along the same scanning locus; and
   in the inspecting of the welded state, the welding state of the welded portion of the workpieces is inspected based on a periodicity of the intensity change of the returned light beam at the time when the welding laser beam is radiated along the same welding locus or at the time when the inspection laser beam is radiated along the same scanning locus.

5. The welded portion inspection method according to claim 4, wherein:
   in the radiating of the welding laser beam or the inspection laser beam, the welding laser beam is radiated along the same welding locus or the inspection laser beam is radiated along the same scanning locus at an unique period of the intensity change of the returned light beam which is obtained when the welding state of the welded portion of the workpieces is normal.

6. The welded portion inspection method according to claim 4, wherein:
   in the inspecting of the welded state, the welding state of the welded portion of the workpieces is inspected by performing Fourier transform or differentiation on an intensity of the returned light beam.

* * * * *